US012685631B2

(12) United States Patent
Yacoub

(10) Patent No.: US 12,685,631 B2
(45) Date of Patent: *Jul. 21, 2026

(54) EXPANDABLE AORTIC OR PULMONARY ROOT

(71) Applicant: Heart Biotech Nano Limited, Winchester (GB)

(72) Inventor: Magdi Yacoub, Winchester (GB)

(73) Assignee: Heart Biotech Nano Limited, Winchester (GB)

( * ) Notice: Subject to any disclaimer, the term of this patent is extended or adjusted under 35 U.S.C. 154(b) by 336 days.

This patent is subject to a terminal disclaimer.

(21) Appl. No.: 17/683,031

(22) Filed: Feb. 28, 2022

(65) Prior Publication Data

US 2022/0233306 A1 Jul. 28, 2022

Related U.S. Application Data

(63) Continuation of application No. 16/383,366, filed on Apr. 12, 2019, now Pat. No. 11,291,541.

(30) Foreign Application Priority Data

Apr. 13, 2018 (GB) ...................................... 1806097

(51) Int. Cl.
*A61F 2/24* (2006.01)
*A61F 2/06* (2013.01)
(Continued)

(52) U.S. Cl.
CPC .............. *A61F 2/2418* (2013.01); *A61F 2/06* (2013.01); *A61F 2/2415* (2013.01); *A61L 27/26* (2013.01);
(Continued)

(58) Field of Classification Search
CPC ................ A61F 2/06; A61F 2210/0076; A61F 2250/0018; A61F 2250/0039; A61F 2/2412; A61F 2250/0017; A61F 2/2418
See application file for complete search history.

(56) References Cited

U.S. PATENT DOCUMENTS

| | | | |
|---|---|---|---|
| 5,769,884 A | 6/1998 | Solovay | |
| 6,319,264 B1 | 11/2001 | Tormala et al. | |
(Continued)

FOREIGN PATENT DOCUMENTS

| | | | | |
|---|---|---|---|---|
| EP | 955019 A2 * | 11/1999 | ............... | A61F 2/06 |
| WO | 0235989 A2 | 5/2002 | | |
(Continued)

OTHER PUBLICATIONS

Search Report issued from the United Kingdom Patent Office for Application No. GB1806097.0 dated Oct. 18, 2018 (8 pages).
(Continued)

*Primary Examiner* — Brian E Pellegrino
(74) *Attorney, Agent, or Firm* — Michael Best & Friedrich LLP

(57) ABSTRACT

A support layer for a synthetic root comprises at least a first region and a second region. The pattern, material, density and/or tension of the support layer in the first region is different to that in the second region. The support may be formed from a knitted, woven, braided or 3D-printed material. The support layer may be comprised within a synthetic aortic or pulmonary root. In at least one region the synthetic root may have a multi-layered structure with the support layer disposed between an inner and an outer nanofiber layer.

15 Claims, 4 Drawing Sheets

(51) Int. Cl.
    *A61L 27/26*         (2006.01)
    *A61L 27/50*         (2006.01)
(52) U.S. Cl.
    CPC ..... *A61L 27/507* (2013.01); *A61F 2210/0076*
        (2013.01); *A61F 2220/0008* (2013.01); *A61F*
        *2240/001* (2013.01); *A61F 2250/0018*
        (2013.01); *A61F 2250/0039* (2013.01); *A61F*
        *2250/0067* (2013.01)

(56) References Cited

U.S. PATENT DOCUMENTS

| | | | | |
|---|---|---|---|---|
| 11,291,541 | B2 * | 4/2022 | Yacoub | .................... A61F 2/06 |
| | | | | 623/1.44 |
| 2005/0052649 | A1 | 3/2005 | Tsujita | |
| 2005/0070992 | A1 | 3/2005 | Bolduc | |
| 2007/0038290 | A1 * | 2/2007 | Huang | .................... A61F 2/90 |
| | | | | 623/1.22 |
| 2009/0299469 | A1 | 12/2009 | Kollar | |
| 2011/0112620 | A1 | 5/2011 | Du | |
| 2014/0207248 | A1 | 7/2014 | Wang et al. | |
| 2016/0317295 | A1 * | 11/2016 | Jana | ................... A61L 27/3895 |
| 2016/0331528 | A1 * | 11/2016 | Parker | .................. A61F 2/2412 |
| | | | | 623/2.14 |

FOREIGN PATENT DOCUMENTS

| | | |
|---|---|---|
| WO | 2008083767 A1 | 7/2008 |
| WO | 2010024880 A1 | 3/2010 |
| WO | 2011134070 A1 | 11/2011 |
| WO | 2011153340 A2 | 12/2011 |

OTHER PUBLICATIONS

Search Report issued from the European Patent Office for Application No. 19169078.3 dated Sep. 4, 2019 (8 pages).

* cited by examiner

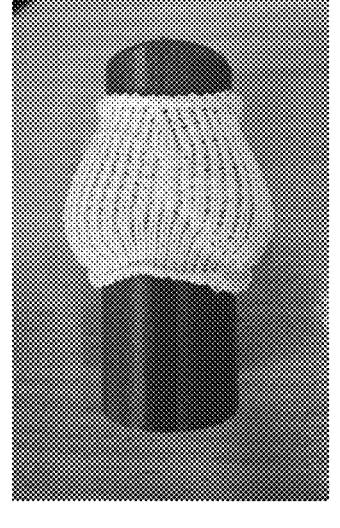
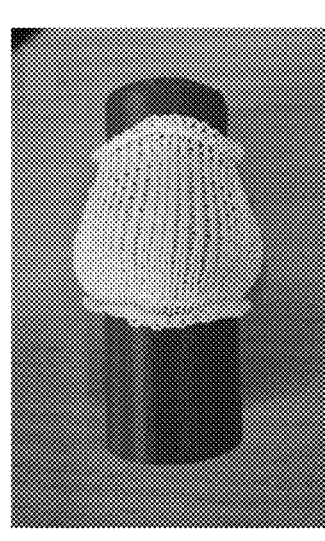
FIG. 3A                              FIG. 3B
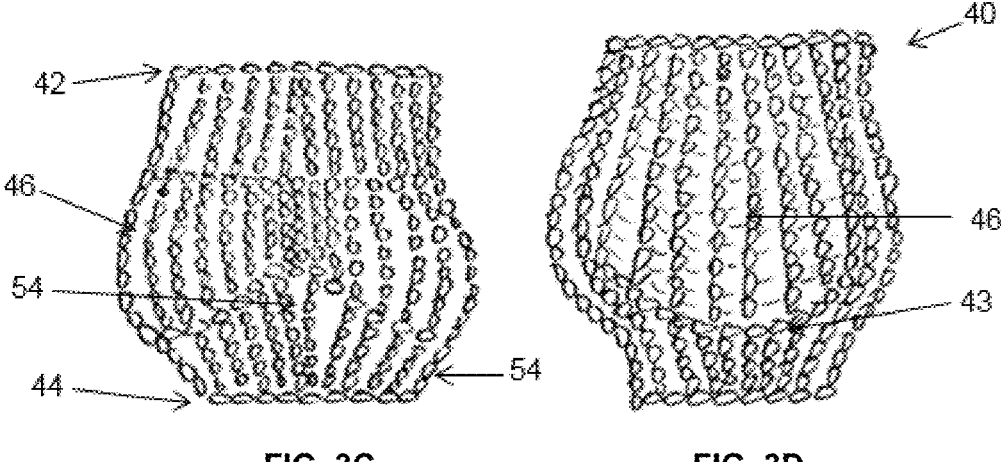
FIG. 3C                              FIG. 3D

EXPANDABLE AORTIC OR PULMONARY ROOT

CROSS-REFERENCE TO RELATED APPLICATION(S)

This application is a continuation of U.S. patent application Ser. No. 16/383,366, filed Apr. 12, 2019, which claims priority to United Kingdom Patent Application No. 1806097.0, filed on Apr. 13, 2018, and the entire contents of which each are hereby incorporated by reference.

TECHNICAL FIELD

The present invention relates to a synthetic root, a method for making the synthetic root, and a support layer for a synthetic root. The invention further relates to a tissue engineered aortic or pulmonary root.

BACKGROUND TO THE INVENTION

Heart valve disease remains a significant cause of morbidity and mortality worldwide. The incidence of this condition is predicted to increase significantly over the next 50 years due to effects of an aging population. Current treatments rely heavily upon replacement of diseased heart valves, despite the fact that currently available valve substitutes have significant limitations, including the tendency to degenerate, calcify and an inability to adapt or grow with the patient. Although prosthetic valve replacement is a common and efficient procedure, a need for alternative solutions exists, especially for children who require valve growth and therefore a living prosthetic. Tissue engineering, which aims to create new and functional living tissues by creating intelligent supporting structures (scaffolds), capable of attracting, housing and instructing host cells, and has great potential to provide such advanced prostheses.

It is hoped that these limitations can be overcome with the use of tissue engineering strategies to produce a living heart valve that will replicate the structure and function of the native valve.

Heart valves (specifically semilunar valves) are extremely sophisticated structures that serve to preserve the unidirectional flow of blood out through the heart, and to optimize coronary and systemic blood flow to different organs. The complexity of aortic valve function was illustrated in 1999 when Yacoub et al. proposed that the function of the valve relies on "dynamism and crosstalk". Dynamism is defined by the ability of the component parts of the valve to move spatially and change their size and shape in a coordinated manner (Yacoub et al., "The aortic outflow and root: a take of dynamism and crosstalk". *The Annals of thoracic surgery.* 1999; 68). The components that form the root (FIG. 1) include the crown shaped annulus, the aortic valve leaflets or cusps, interleaflet triangles, and the supravalvular regions (sinus of Valsalva and the sinotubular junction).

These structures move in a coordinated manner in a passive (in response to hemodynamic forces) and dynamic (cellular and neuronal mechanisms) manner during each cardiac cycle to minimize stress on valve components and to enhance durability.

Three-dimensional biomaterial scaffolds that support cell infiltration and tissue organization have been extensively investigated for applications in regenerative medicine and tissue engineering (Yacoub, Magdi H. "In search of living valve substitutes." (2015): 889-891). Closely mimicking the extracellular matrix (ECM) at the nanometer level is still, however, a challenge. The ECM is a complex and dynamic structure secreted by cells to provide the structure and properties of a tissue, as well as to attract and instruct the appropriate type of cell. The main component of the ECM includes a system of molecules capable of supporting as well as regulating cellular functions. One such molecule is collagen, which is capable of regulating both functions.

Collagen-based biomaterials for use in tissue engineering are commercially available. Typically, commercial collagens are extracted from a mammalian source, decellularized, purified and sterilized. However, the use of mammalian-derived collagen presents potential hazards, including contagion through the transmission of pathogens. It is therefore desirable to engineer artificial tissues using synthetic scaffolds which mimic natural collagen networks.

Although prosthetic valve replacement is a common and efficient procedure, a need for alternative solutions exists, especially for children who require valve growth and therefore a living prosthetic. Tissue engineering, which aims to create new and functional living tissues by the in vitro association of supportive structure (scaffolds) and cells, has great potential to provide such advanced prostheses.

Although synthetic nanofibre matrices are known, most of these are limited to simple geometries such as a flat sheets or tubular structures. To apply these matrices such that they function as a heart valve often requires the use of a stent or suture ring to provide a structural support. The stent or sewing ring occupies the space in patient's annulus, therefore increases turbulence, pressure and enhances stress on the leaflet during closure and reduces valve orifice area. Therefore, the use of a stentless scaffold is preferred.

Known methods for the production of scaffold material for the tissue engineering of heart valves either focus on the production of cusp material (for use in a stented valve) or the production of valve cusps, suspended within an outflow tract that serves to mimic the native root structure. However, the known methods do not result in the production of a complete valve mechanism that mimics the native valve and provides dynamism of each component part in a specific manner.

The present invention has been devised with these issues in mind.

SUMMARY OF THE INVENTION

According to a first aspect of the invention there is provided a support layer for a synthetic root, the support layer comprising at least a first region and a second region wherein the pattern, material, density and/or tension of the support layer in the first region is different to that in the second region.

The support layer may be formed of a knitted, woven, braided or 3D-printed material.

The pattern, material, density and/or tension may affect the stiffness or elasticity of the support layer. These parameters, individually or in any combination, may be used to control the stiffness or elasticity of the different regions of the support layer. The stiffness or elasticity of the support layer can therefore be tailored in each region to optimize function.

Thus, according to a second aspect of the invention there is provided a support layer for a synthetic root, the support layer comprising at least a first region and a second region wherein the stiffness of the support layer in the first region is different to the stiffness of the support layer in the second region.

According to a third aspect of the invention there is provided a synthetic root comprising the support layer of the first aspect.

As used herein, the term "synthetic" will be understood as meaning that the root of the invention is artificial, or engineered, as opposed to a natural root. However, it will be appreciated that a synthetic root in accordance with certain aspects of the invention may comprise living tissue or cells which have colonized the engineered structure of the root. Thus, in some aspects of the invention the root is not wholly made-made, and may comprise living components. The root of the invention may also be described as an "engineered root".

In some embodiments the synthetic root comprises, at least in some regions, the support layer and at least one additional layer. The at least one additional layer may be provided on the interior of the support layer, such that the support layer is not in contact with blood, when in use. In some embodiments, two or more additional layers may be provided, at least in some regions of the root. For example, the synthetic root may comprise, in at least some regions, the support layer disposed between an inner and an outer layer.

The synthetic root may comprise, at least in some regions, a multi-layered structure comprising the support layer disposed between an inner and an outer nanofiber layer. However, it will be appreciated that not all of the regions of the synthetic root are required to have this multilayered structure. For example, some regions may comprise a single layer, or only nanofiber layers. In some embodiments, the synthetic root comprises at least two regions, wherein in at least one region the graft has a multi-layered structure comprising the support layer disposed between an inner and an outer nanofiber layer.

It will therefore be understood that the synthetic root of the invention is non-uniform in its structure and/or mechanical properties. The different regions or portions of the synthetic root have different structures, properties and/or functionalities, which may correspond to the different anatomical regions of a natural root. The multi-layered structure of the synthetic root enables variation in the mechanical properties of the synthetic root for each region through variation in the design and/or material of the support layer and/or the nanofiber layers. This allows the synthetic root of the invention to more closely mimic the function of natural tissue, compared to prior art grafts which are uniform in their structure and properties.

The synthetic root of the invention comprises different regions or zones with different properties and functions. Each region may provide a specific valve function. In some embodiments the synthetic root comprises a first region and at least a second region. In some embodiments the synthetic root comprises three, four, five, six or more regions.

The synthetic root may be an aortic or pulmonary root. The root may comprise at least two or a plurality of regions corresponding in shape, size and/or function to two or more of the following anatomical regions of a natural root: annulus, interleaflet triangles, leaflets (cusps), sinuses, and sinotubular junction. In some embodiments, the root comprises all of these regions. Thus, the support layer may be for use in an aortic or pulmonary root.

In some embodiments, the synthetic root further comprises one or more additional regions corresponding in shape, size and/or function to anatomical features selected from: ascending artery; Left Ventricular Outflow Tract connection; pulmonary artery; aortic artery; and Right Ventricular Outflow Tract connection.

In some embodiments, the support layer and/or the synthetic root is approximately tubular in shape. The support layer and/or the synthetic root may have a tubular structure comprising a first end and a second end.

In embodiments wherein the support is knitted, braided or woven, the first end may be formed by a first (top) sewing ring. The second end may be formed by a second (bottom) sewing ring. The sewing ring(s) may be used to attach the root of the invention to the natural heart tissue.

Between the ends of the tube there may be a region of increased diameter. This region may be formed by at least one outwardly protruding portion, or bulge. Preferably three outwardly protruding portions (or bulges) are arranged around the circumference of the tube. The outwardly protruding portions may have a curved profile. These portions correspond to the sinus regions of a pulmonary or aortic root. It will be understood that the degree of curvature of the bulges can be optimized by the skilled person according to the patient, to allow health blood flow.

The region of increased diameter (i.e. the sinus region) may be defined by an upper boundary which is proximal to the first end of the support layer/root, and a lower boundary which is proximal to the second end of the support layer/root. The upper boundary may be considered to correspond to the sinotubular junction.

Between the second end and the region of increased diameter, a crown-shaped region may be provided. The crown-shaped region may comprise three triangular portions connected by a base of circular cross-section. Each triangular portion may extend between two adjacent outwardly protruding portions which form the sinus regions. The triangular portions correspond to the interleaflet triangles of a pulmonary or aortic root.

In some embodiments, the synthetic root comprises one or more leaflets which project inwardly into the tube. In some embodiments the root comprises two or three leaflets (e.g. forming a bicuspid or tricuspid valve). These leaflets correspond to the cusps. Like in a natural root, the leaflets may have a semilunar (half-moon) shape. The leaflets are attached to the interior of the tube.

The support layer and/or the synthetic root may have a height (i.e. the distance from the first end to the second end) of from 4 to 8 cm, or from 5 to 7 cm. However, it will be appreciated that the size of the support layer and/or the vascular can be tailored by the skilled person to the patient. For example, if the synthetic root is intended for use in an infant, the dimensions will be modified accordingly.

The diameter of the synthetic root will vary along its length, but is typically in the range of 1 to 6 cm. The maximum diameter of the region of increased diameter (corresponding to the mid-sinus region) may be from 3 to 5 cm. At the upper and lower boundaries of the region of increased diameter, the diameter of the root may be from 1.5 to 4.0 cm, from 2.0 to 3.5 cm or from 2.5 to 3.0 cm.

The specific mechanical properties of each region or functional component of the graft may be achieved by modulating the structural features, such as the material, thickness, density, elasticity and/or fibre orientation of the nanofiber layers, and/or the material, pattern, thickness, density and/or elasticity of the support layer. Thus, differences between the regions are realized by variations in one or more layers of each region.

In some embodiments, the stiffness of the first region is different to the stiffness of at least the second region. In some embodiments, the stiffness of the outwardly protruding portions, corresponding to the sinuses, is different to the stiffness of the crown-shaped region. The triangular portions of the crown-shaped region correspond to the interleaflet triangles.

It will be appreciated that the anatomical stiffness (in the physiological strain) of the different regions of the graft may be selected as appropriate, for example according to whether the synthetic root is for an adult or a child, in order to prevent dilation.

In some embodiments, the synthetic root is partially or completely biodegradable.

The synthetic root may be capable of cell colonization. This allows complete remodeling of the root in vivo into functional tissue.

According to a fourth aspect of the present invention, there is provided a tissue engineered root comprising the support layer of the first aspect of the invention, at least one nanofiber layer, and wherein the root has been at least partially colonized by cells.

At least in some regions, the tissue engineered root comprises a multi-layered structure wherein the support layer disposed between an inner and an outer nanofiber layer.

Thus, in certain embodiments the present invention provides a tissue-engineered free-standing, stentless aortic or pulmonary root that is anatomically similar in shape and/or size to a natural human root, having a tricuspid semilunar valve configuration comprising regions corresponding to sinuses, an annulus, interleaflet triangles, a sinotubular junction and leaflets (cusps). By reproducing the anatomical shape of the natural human root, the invention allows dynamic physiological enlargement of the annulus during the cardiac cycle, sustaining physiological pulsatile flow. The tissue engineered root and valve of the invention may be a composite structure comprising a support layer and at least one additional layer.

It will be appreciated that any statements made herein in relation to the first, second, third or further aspects of the invention may be combined with any other aspect of the invention as appropriate.

Support Layer

The support layer may be formed of a knitted, braided or woven material. Preferably the support layer is knitted. In some embodiments the support layer is 3D-printed.

In embodiments wherein the support layer is 3D-printed, it will be appreciated that differences in the properties (e.g. stiffness) between the regions can be achieved by varying the structure of the printed support layer between those regions. For example, in a first region the support layer may be printed having a pattern formed of relatively thinner struts, whereas in a second region the support layer may have a pattern formed of relatively thicker struts.

The support layer must maintain the correct shape of the synthetic root, while providing the required mechanical and elongation properties in the different regions of the synthetic root. These properties may be achieved through different tensions in the material forming the support layer in the different regions. The differing tensions may be achieved through the use of differing knitting, braiding, printing or weaving patterns. The multi-layered structure of the synthetic root thus enables variation in the mechanical properties of the valve for each region through the design and/or material of the support layer and the nanofiber layers.

The support layer may comprise at least first and second regions, of differing stiffness. The difference in the stiffness between the first and second regions may be achieved through the use of a different pattern, material, density and/or tension in these regions. It will be appreciated that, in some embodiments depending on the type of material and the pattern, the higher the density of stitches and/or the higher the tension, the higher the stiffness of the region.

In at least one region of the synthetic root, the support layer is sandwiched between the inner and outer nanofiber layers. The support layer provides structural integrity and enables the mechanical functions of the synthetic root to be achieved until it is replaced by in vivo cell colonisation. These mechanical functions may include providing stiffness, thereby controlling excess dilation.

The support layer may be for an aortic or pulmonary root.

In some embodiments the support layer is formed from a knitted, woven or braided yarn. The yarn may be formed from a polymer. Suitable polymers include PCL, polyester, PLA, PLGA, silk (poly(dioxanone), poly(ortho esters), poly (amide esters), poly(anhydrides), polyvinyl esters, (poly (tetrafluoroethylene), poly(ethylene), poly(ethylene glycol), polypropylene oxide, or combinations thereof.

In some embodiments, the yarn comprises or consists of PCL. A PLC yarn may further comprise polyester and/or carbon fibres.

In some embodiments the yarn has a decitex (dtex) of from 150 to 270, from 180 to 250 or from 200 to 230 (e.g. about 220).

In some embodiments wherein the support is formed of a knitted material, the knit pattern of the outwardly protruding portion(s) may be different to that of one or more other regions of the support. Tuck stitches may be used to generate the curved lower boundary of the outwardly protruding portions corresponding to the sinuses.

In some embodiments, the tension of the material of the outwardly protruding portion(s), corresponding to the sinus region(s), is higher than the tension in one or more of the other regions of the support, for example in the regions corresponding to the annulus and/or the sinotubular junction.

In the region of the support layer corresponding to the sinuses, the tension may be from 10 to 12. In the region corresponding to the annulus the tension may be from 6 to 18.

In some embodiments, the pattern of the outwardly protruding portion(s), corresponding to the sinus regions, is different to one or more of the other regions of the support. The pattern in the sinus regions may be different to that of the rest of the support.

In some embodiments, the support layer comprises an additional knitted portion of the same or similar material. The additional knitted portion may form an additional layer of the support. Alternatively, it may form an extension of the support layer.

In some embodiments the additional knitted portion may be tubular in shape. For example, this portion may serve as a sewing ring for attaching the synthetic root to the host tissue, or it may strengthen an existing sewing ring in the support layer. The size and shape of the additional knitted portion may be configured to fit the elliptical shape of an outflow tract. The additional knitted portion may be integrally formed with the support layer. Alternatively, the additional knitted portion may be formed separately and attached to the support layer to form a composite. The additional knitted portion may have a tension of from 6 to 10. The use of a lower tension knit gives the structure a greater density.

In one or more regions, the support layer may be bonded to one or both of the inner and outer nanofiber layers. Bonding may be achieved by solvent welding, heat melting or other mechanical or chemical joining techniques. This provides structural integrity to the synthetic root, but does not affect cell colonization or the movement of gases and macronutrients.

Nanofiber Layers

The inner nanofiber layer and/or the outer nanofiber layer may comprise or consist of a polymer. The polymer may be synthetic. It is preferred that the polymer is biocompatible. In some embodiments the polymer is biodegradable. Suitable polymers include polycaprolactone (PCL), polyester, (poly(dioxanone), poly(ortho esters), poly(amide esters), poly(anhydrides), polyvinyl esters, (poly(tetrafluoroethylene), poly(ethylene), poly(ethylene glycol), polypropylene oxide, polylactic acid (PLA), poly(lactic-co-glycolic acid (PLGA), silk, or combinations thereof.

In some embodiments the inner and/or outer nanofiber layer comprises PCL, or a PCL composite. PCL is advantageous in that it is biocompatible and biodegradable, has good mechanical properties, and a slow rate of degradation.

The nanofibers layers may be formed by jet spraying and/or electrospinning nanofibers.

The nanofibers may be from 10 nm to 1500 nm in length.

The nanofibers of the inner and/or outer nanofiber layers may be aligned. The fibres may be aligned with the other fibers within the same region. In some embodiments, the fibres are aligned across the whole synthetic root. In some embodiments "aligned" is understood to mean that than 50%, more than 60% or more than 70% of the nanofibers have an orientation which does not diverge by more than 20 degrees, by more than 15 degrees or by more than 10 degrees (positive or negative) from the average (median) orientation. By aligning the fibers the resulting material will have anisotropic properties similar to those of human heart valve tissue.

The inner and/or outer nanofiber layers may be decorated with molecules. The molecules may be bioactive. By "bioactive", it will be understood that the molecules have a biological effect on living tissue or cells. For example, the molecules may be capable of specifically attracting endothelial progenitor cells from the blood in preference to other circulating cells. Additionally, or alternatively, the nanofiber layers may be decorated with bioactive molecules which are capable of attracting extracellular matrix proteins, and/or enhancing cell function or tissue formation. In some embodiments, the nanofiber layers are decorated with molecules having anti-calcification properties. The nanofiber layers may be decorated with two or more different bioactive molecules which perform different functions. The grafting of the bioactive molecules on to the nanofiber surface may be achieved through carbodimide chemistry, bifunctional crosslinkers or other suitable covalent attachment methods which will be known to those skilled in the art.

In some embodiments the molecules are peptides. The peptides may comprise sequences which selectively bind progenitor cells. In some embodiments, the peptides comprise the sequence TPSLEQRTVYAK.

In some embodiments, the molecules comprise a PEG crosslinker. This provides an anti-fouling property.

The nanofiber layers provide a porous and cell-penetrable matrix which encourages cell colonization and promotes synthesis of a natural extracellular matrix. The alignment of fibres within these layers enables natural anisotropic mechanical properties to be replicated. Thus, unlike the artificial valves of the prior art, the synthetic root of the invention is able to grow and actively re-mode over time in vivo into functional tissue, thereby producing a living root. The synthetic root is able to mimic and coordinate the natural biological functions until the synthetic components biodegrade and are replaced by living tissue.

The median pore size of the inner and/or outer nanofiber layers may be from 50 to 110 μm, from 70 to 100 μm, or from 80 to 90 μm. In some embodiments, the pore size is at least 60 μm, at least 70 μm, at least 80 μm or at least 90 μm.

In some embodiments, the porosity of the inner and/or outer nanofiber layer is from 95 to 99%, or from 96% to 98%. A matrix which can be more easily colonized by cells is beneficial for the formation of homogeneous tissue.

Annulus

As used herein, the annulus is the crown-shaped region below the curved, lower boundary of the outwardly protruding portions (sinus regions).

Studies have shown that in natural heart valves the annulus changes its size during the cardiac cycle from circular during systole to elliptical during diastole. This has the overall effect of reducing the resistance to emptying of the left ventricle during systole and lowering the stress of the aortic cusps during diastole by reducing the overall area of the aortic orifice.

In embodiments of the present invention, in the annulus region or component of the root the outer and/or inner nanofiber layers may have an anisotropic structure. The anisotropy of the nanofibers may be achieved through a jet-spraying process for forming the nanofibers layers. For example, the rotational speed used to collect the fibres may help to control the degree of alignment and thus the mechanical properties of the layer. The properties of the outer and/or inner nanofiber layers may be modulated through the orientation of the fibres, the degree of alignment, the fibre density, the thickness of the layers and/or their porosity.

However, it is preferred that the mechanical properties of the annulus are conferred mainly by the support layer.

The support layer may maintain a correct elliptical shape (in cross section) of the annulus. Thus, in the region corresponding to the annulus, the tubular support layer may be elliptical in cross section. At the same time, the support layer may provide mechanical and elongation properties that enable elasticity perpendicular to the elliptical axis, allowing and limiting the dilation of the annulus to a circle during diastole. These properties may be achieved through different tensions of the support structure around the circumference of the annulus. Thus, in a region corresponding to the annulus, the support may have a tension of from 6 to 18, from 7 to 16 or from 8 to 14.

Sinuses

The sinuses of a natural heart valve have a defined curvature, which support vortices in diastole. It has been shown both in vitro and in vivo that the vortices of the sinuses have the effect of closing the valves in a smooth fashion from side to side. Changes in the size and shape of the aortic sinuses at the sinotubular level plays a major role in producing aortic regurgitation in a patient with dilation of the aortic root.

In some embodiments, a tubular synthetic root and/or support layer in accordance with the invention may comprise a region of increased diameter. This region may be formed by at least one outwardly protruding portion, or bulge. Preferably three outwardly protruding portions (bulges) are arranged around the circumference of the tube. The outwardly protruding portions may have a curved profile. These portions correspond to the sinus regions of a pulmonary or aortic root.

In embodiments of the invention, the size and shape of the support layer and/or the synthetic root in the regions corresponding to the sinuses is selected in accordance with those of a natural root, based on average physiological values obtained by, for example, MRI.

In the sinus regions, the synthetic root may comprise the support layer between inner and outer nanofiber layers.

In the sinus regions, the support layer may function to reinforce the freestanding valve during the cardiac cycle. In some embodiments, the support layer in the sinus regions has a higher tension than the support layer in the other regions of the root. A higher tension in the region of the sinus may be achieved by varying the pattern of a knitted, braided or woven support layer. For example, the sinus region may have a tension of 10 or 11. This tension may be higher than that of the annulus and sinotubular regions. Tuck stitches may be used to generate the curvature of the sinuses.

As will be known by the skilled person, the stiffness of the various components of the support or graft can be determined using equibiaxial or biaxial mechanical testing (Pham et al., Acta Biomaterialia (2017); vol. 54: pages 345-355; Matthews et al., (2010), Annals of Thoracic Surgery (2010); 89: pages 1981-1989). The stiffness value may be that measured at 30% strain, which is generally considered to correspond to physiological strain.

The stiffness of the region of the support or root which corresponds to the sinus region may be determined using biaxial mechanical testing. In some embodiments, the stiffness of the sinus region is from 0.1 to 0.5 MPa in the circumferential and/or radial direction.

In some embodiments, the stiffness of region of the support or root which corresponds to the pulmonary sinuses is from 0.13 MPa to 0.40 MPa in a circumferential direction. In some embodiments, the stiffness of region of the support or root which corresponds to the pulmonary sinuses is from 0.1 MPa to 0.47 MPa in a radial direction.

The stiffness of region of the support or root which corresponds to the aortic sinuses may be from 0.11 MPa to 0.5 MPa in a circumferential direction and/or radial direction.

Sinotubular Junction and Arteries

The stiffness of the region of the support or root which corresponds to the sinotubular junction, and optionally an adjacent region corresponding to the artery area, may be no greater than 0.5, 0.3 or 0.1 MPa in the circumferential direction. In some embodiments, the region of the support or root which corresponds to the stiffness of the sinotubular junction, and optionally its adjacent artery area, is no greater than 0.4, 0.2 or 0.08 MPa in the radial direction.

The stiffness of region of the support or root which corresponds to the artery above the sinotubular junction may be determined using biaxial mechanical testing. Stiffness may be measured at 30% strain. The stiffness of the artery may be from 0.05 to 0.5 MPa.

In some embodiments, a region of the support or root which corresponds to the pulmonary artery has a stiffness of from 0.05 MPa to 0.3 MPa, e.g. from 0.06 MPa to 0.25 MPa in a circumferential direction. In some embodiments, a region of the support or root which corresponds to the pulmonary artery has a stiffness of from 0.05 MPa to 0.2 MPa, e.g. from 0.06 MPa to 0.195 MPa in a radial direction.

In some embodiments, a region of the support or root which corresponds to the aortic artery has a stiffness of from 0.1 to 0.5 MPa or from 0.15 to 0.45 MPa (e.g. from 0.157 MPa to 0.466 MPa) in a circumferential direction. In some embodiments, a region of the support or root which corresponds to the aortic artery has a stiff of from 0.1 to 0.4 MPa or from 0.12 to 0.38 MPa (e.g. from 0.134 MPa to 0.379 MPa) in a radial direction.

Interleaflet Triangles

In the natural heart, the dynamism of the root depends to a large extent on the interleaflet triangles, which act as hinges and vary in shape and size in individual valves. It is therefore desirable that the function of these structures is preserved in a synthetic root.

In the root and the support layer of the invention, approximately triangular regions may be formed between adjacent outwardly protruding portions, these triangular regions corresponding to the interleaflet triangles. In these regions, the synthetic root may comprise the support layer between inner and outer nanofiber layers.

In some embodiments, the regions corresponding to the interleaflet triangles are thinner and/or less stiff than the sinuses. This allows the connected sinuses to work efficiently.

In some embodiments the regions corresponding to the interleaflet triangles comprise a hydrogel. The hydrogel may be comprised within the support layer. This enables a higher degree of elasticity to be achieved.

Cusps

A tubular synthetic root in accordance with the invention may comprise inwardly projecting leaflets, which provide the function of cusps. It will therefore be appreciated that the terms "leaflet" and "cusps" may be used interchangeably.

The cusps play a major role in the function of the aortic root. It is recognized that the curvature of the cusps plays an important part in reducing the stress on the cusps. The length of the free edge of the cusps also plays an important role in aortic valve function, and increased length of the free edge can result in prolapse of the cusp during diastole.

The leaflets may be formed from one or more layers of nanofibres. In some embodiments, each leaflet is formed from a single nanofiber layer. The nanofiber layer may include knitted fibres. In some embodiments, the leaflets do not comprise the support layer. In alternative embodiments the leaflets comprise the support layer, optionally with inner and outer nanofiber layers.

The properties of the leaflets may be modulated through the degree of fibre alignment, the fibre density, the thickness of the nanofiber layers and/or their porosity.

The shape of the leaflets may be achieved using a structure (e.g. a 3D printed structure) to support the nanofibillar layer(s).

In embodiments of the invention, in the leaflets the nanofiber layer(s) has an anisotropic structure. Thus, the inner and/or outer nanofiber layers are highly aligned in the leaflets. This helps the synthetic root to mimic natural cusp anisotropy, reduce shear stress on the cusps, enhance competence and reduce resistance to flow.

In some embodiments, the nanofibers have a greater degree of alignment aligned in the leaflets compared to other regions of the root. In the leaflets the nanofibers may be aligned in the circumferential direction.

The anisotropy (i.e. alignment) of the nanofiber layers may be controlled by using jet spraying technology, and by modifying the rotational speed used to collect the fibres. The higher degree of alignment in the leaflets compared to in other layers may help the synthetic root to mimic natural cusp anisotropy, reduce shear stress on the cusps, enhance competence and reduce resistance to flow. The alignment of the nanofibers in the leaflets may be achieved through jet-spraying during formation of the nanofiber layers.

As will be appreciated by a skilled person, the thickness of the nanofiber layer in the leaflets (or any other region) is determined by factors including the rate of polymer supply and duration of spraying.

The natural shape and length of the synthetic root in the leaflets may be achieved through digital manufacturing technology such as 3D printing. The size and shape of the cusps may be selected in accordance with those of a natural root, based on average physiological values obtained by, for example, MRI.

In some embodiments the leaflets (i.e. cusps) have a coapting length of at least 3 mm.

The stiffness of the leaflets may be determined using equibiaxial mechanical testing and results in stress-strain curves in radial and circumferential direction of the leaflets. The high tangent region of the stress—strain curve for each direction of the leaflets may be used as a measurement of the stiffness of the leaflet.

The stiffness of the leaflets may be from 2 to 18 MPa, or from 3 to 15 MPa.

In some embodiments, a region of the support or root which corresponds to the pulmonary cusp (i.e. the cusp of a pulmonary root) has a stiffness of from 2 to 10 MPa or from 3 to 9 MPa (e.g. from 3.3 MPa to 8.6 MPa) in the circumferential direction. In some embodiments, the region of the support or root which corresponds to the pulmonary cusp has a stiffness of from 0.8 MPa to 5 MPa or from 1.0 to 4 MPa (e.g. from 1.2 MPa to 3.3 MPa) in the radial direction.

In some embodiments, a region of the support or root which corresponds to the aortic cusp (i.e. the cusp of an aortic root) has a stiffness of from 6 to 16 MPa or from 8 to 15 MPa (e.g. from 8.8 MPa to 14.7 MPa) in a circumferential direction. In some embodiments, the region of the support or root which corresponds to the aortic cusp has a stiffness of from 1.5 to 4 MPa or from 1.8 to 3.5 MPa (e.g. from 2 MPa to 3.4 MPa) in the radial direction.

Each leaflet may be connected to the sinus region by a hinge.

Hinge

In a natural heart, the dynamism of the root components not only depends on the properties of each individual component, but is also largely dependent on the sophisticated interaction between the different component parts. The flexural hinge mechanism between the sinuses and the cusps has to: allow the expansion of the annulus and sinuses over the cardiac cycle; enable cusp opening and closure, as well as shear stress distribution; and stability against the pressure gradient between the ventricle and the root.

Thus, in some embodiments the synthetic root comprises a hinge which connects each leaflet to an interior wall of the root.

In some embodiments, the hinge comprise textiles (e.g. PCL yarn), carbon fibers or graphene. For example, a carbon fibre yarn or PCL yarn may be woven into a nanofiber layer. In some embodiments, the hinge comprises a layer of carbon fibers between inner and outer nanofiber layers. In some embodiments, the hinge region comprises the support layer, which may be disposed between inner and outer nanofiber layers. The carbon fibers provide the necessary flexibility and durability of the hinge mechanism for long term implantation of the root.

It will be appreciated that the differences in the mechanical properties of the regions of the support layer/synthetic root (other than the regions corresponding to the cusps) may be primarily defined by the properties of the support structure, in particular its stiffness which varies between the different regions.

Method of Making the Synthetic Root

According to a fourth aspect of the invention there is provided a method for making a synthetic root, comprising:
  forming a first nanofiber layer on a mould;
  placing a support layer on the first nanofiber layer;

forming a second nanofiber layer on the support layer; and
  removing the mould.

The method of the fourth aspect thus produces a synthetic root comprising a support layer disposed between first (i.e. inner) and second (i.e. outer) nanofiber layers. The method of the fourth aspect may therefore be used to produce a synthetic root in accordance with the third aspect of the invention. The support layer may be that of the first or second aspect of the invention.

The first and/or second nanofiber layer may be formed by electrospinning or jet spraying.

In some embodiments, the first and/or second nanofiber layer is formed by spraying a polymer solution onto a rotating mould. It has been found that by spraying a polymer solution onto a rotating drum, a matrix can be produced in which the nanofibres are aligned in the direction of rotation. The matrix of aligned nanofibres is believed to mimic the native anisotropy of heart valves and other tissues.

The degree of alignment of the nanofibres has been found to be a function of the rotation speed. The speed of rotation may be from 8 m/s to 100 m/s, from 10 m/s to 50 m/s, or from 15 to 30 m/s, for example approximately 20 m/s.

The support layer may be made by knitting, braiding, weaving and/or 3D additive manufacturing.

In a further aspect, the invention provides a method of making a support layer, by knitting, braiding, weaving and/or 3D additive manufacturing. The support layer may be that of the first or second aspect of the invention.

In some embodiments, the support layer is made by knitting. A knitted support layer may be made using an industrial knitting machine which is capable of knitting cylindrical tubes of varying ply, sizes, patterns and yarns.

A suitable industrial knitting machine may have a needle density of from 16 to 28 needles per inch. This can achieve the required density of stitches, and the different tensions in different regions of the support structure. A jersey knit pattern may be used. A number of tuck stiches may be inserted at specific points to provide regional shaping and the right tension. In some embodiments, a tension of from 6 to 16 is used in each region of the support structure.

The support layer may be knitted using a knit pattern which is designed to confer specific mechanical properties (such as stiffness) to defined regions or components of the synthetic root. For example, these regions may include the annular region (annulus), the intra-leaflet triangles, the sinuses, the sinotubular junction and/or the aorta or pulmonary (ascending) artery.

The mould may be formed using any appropriate method, such as casting or 3D printing. The shape and size of the mould may be based on a scanned patient image. For example, a scanned image obtained using MRI or CT may be processed using software (such as Mimics) to generate 3D model. The 3D model can then be imported into CAD software (such as Solidworks) to allow modifications for 3D printing.

The mould may be formed from a dissolvable material, for example a dissolvable polymer such as polyvinyl alcohol (PVA). This enables the mould to be easily removed from the finished root. The dissolvable mould may be removed by immersion in a solvent.

In some embodiments, the mould is formed from two or more mould units. The mould may be formed from two, three, four, five or more mould units. The mould units may be assembled together to form the complete mould prior to forming the first nanofiber layer on the mould.

In some embodiments, the method further comprises forming a nanofiber layer on one or more of the separate mould units, before the mould units are assembled to form the complete mould. The mould units may be assembled together in a dissolvable holder.

In some embodiments, the method comprises:

forming a first nanofiber layer on a mould unit;

assembling three or more mould units together to form a complete mould;

optionally, forming a second nanofiber layer on the complete mould;

placing a support layer over the complete mould (i.e. on top of the second nanofiber layer);

forming a third nanofiber layer on the support layer; and removing the mould.

In some embodiments, the method further comprises functionalizing one or more of the nanofiber layers by binding bioactive molecules to the nanofibres. This may also be described as 'decorating' the nanofiber layers. The functionalization of nanofibrillar layers may be achieved through the formation of covalent or non-covalent bonds.

The bioactive molecules may be peptides. The peptides may comprise or consist of short chains of amino acids, for example from 3 to 15 amino acids. In some embodiments, the peptides are capable of binding to cell receptors such as integrins. Examples of peptides that may be used include KQAGDV, LDV, IDS RLD, KRLDGS, RGD, IET, YYGDLR, FYFDLR, YIGSR, REDV, YKVAV, RNI-AEIIKDI, KHIFSDDSSE, VPGIG, FHRRIKA, KRSR and TPSLEQRTVYAK.

The bioactive molecules may be attached to the matrix via a linker. The linker may be attached to the bioactive molecule prior to functionalization of the nanofiber layer(s) or, alternatively, the linker may be attached to the nanofiber layer(s) prior to binding the bioactive molecules to the linker. Thus, in some embodiments, the method comprises functionalizing the nanofiber layer(s) with linker-bioactive molecule conjugates. In other embodiments, the step of functionalizing the nanofiber layer(s) comprises binding linker molecules to the nanofiber layer(s), and then binding the bioactive molecules to the linkers. Examples of suitable linkers include dendritic polymers (also known as "dendrimers" or "dendronized polymers"), in particular poly-ionic dendritic polymers (e.g. poly(amidoamine), poly(ethylenimine), or linear polymers (e.g. poly(acrylic acid)). The linkers may be grafted with a peptide of interest prior to functionalization of the nanofiber layer(s).

The synthetic root of the invention may be used for the treatment of diseased or damaged tissue including heart valves or roots. In particular, the synthetic root of the invention may find use in the treatment of cardiovascular disease, for example heart valve disease. The patient may be animal or human.

The invention further relates to the use of the synthetic root of the first aspect of the invention in therapy or surgery. For example, the synthetic root may be used in the treatment of diseased or damaged tissue. In particular, the synthetic root may be used to treat heart disease.

In some embodiments, the synthetic root may be used in the surgical treatment of complex congenital conditions in infants, such as truncus arteriosus, univentricular heart or the transposition of the great arteries.

Also provided is a method of treatment comprising inserting the synthetic root of the invention into a subject in need thereof. The synthetic root may replace the natural aortic or pulmonary root.

The subject may be a mammal, in particular a human.

It will be understood that the embodiments described above may be applicable to any aspect of the invention, unless otherwise stated.

DETAILED DESCRIPTION

Embodiments of the invention will now be described by way of example and with reference to the accompanying figures, in which.

Figures 4A, 4B:
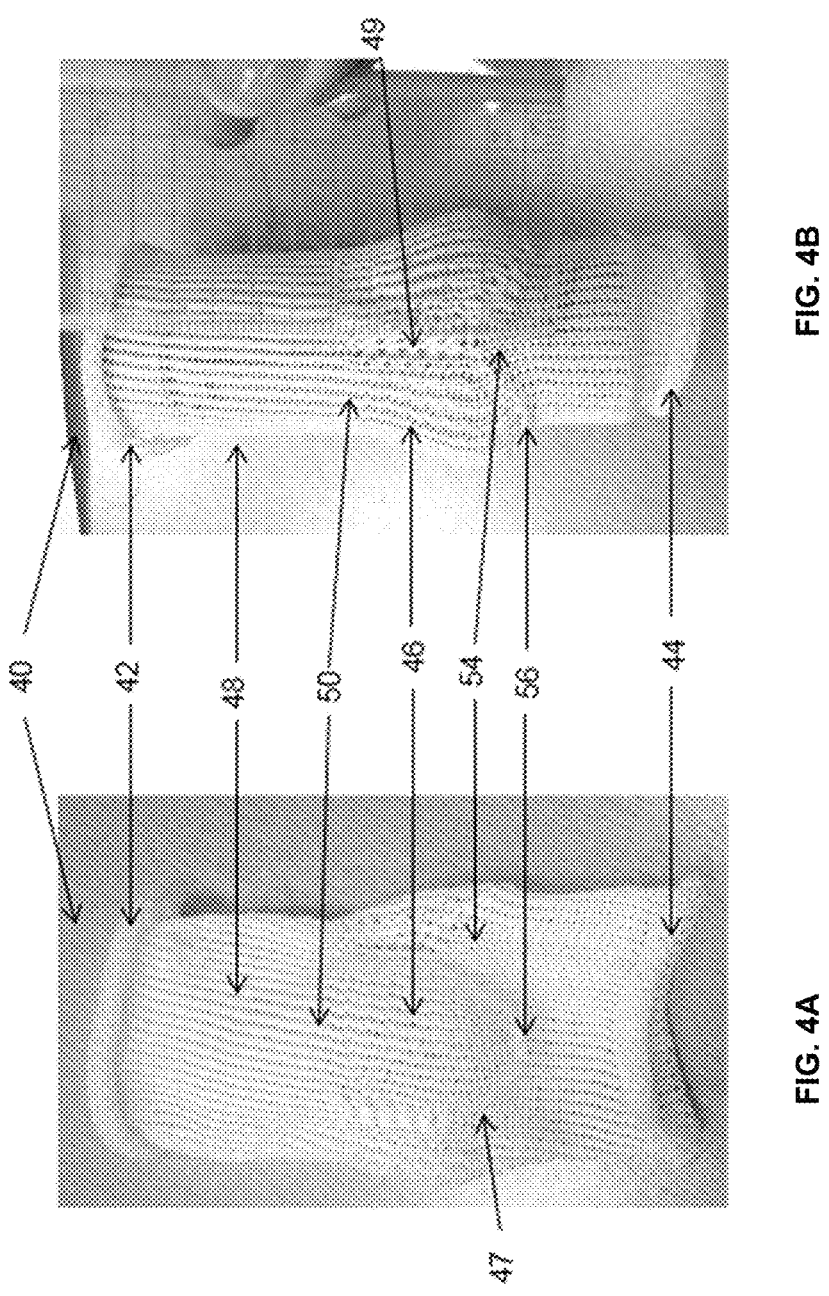

FIG. 3A, FIG. 3B, FIG. 3C, and FIG. 3D show photographs of a knitted support layer in commissural view with 2 bulges (FIG. 3A) and in single bulge view (FIG. 3B), with their representative schematic drawings (FIG. 3C) and (FIG. 3D), respectively; and FIG. 4A and FIG. 4B are photographs of a knitted support layer, according to an embodiment of the invention.

Figure 1:
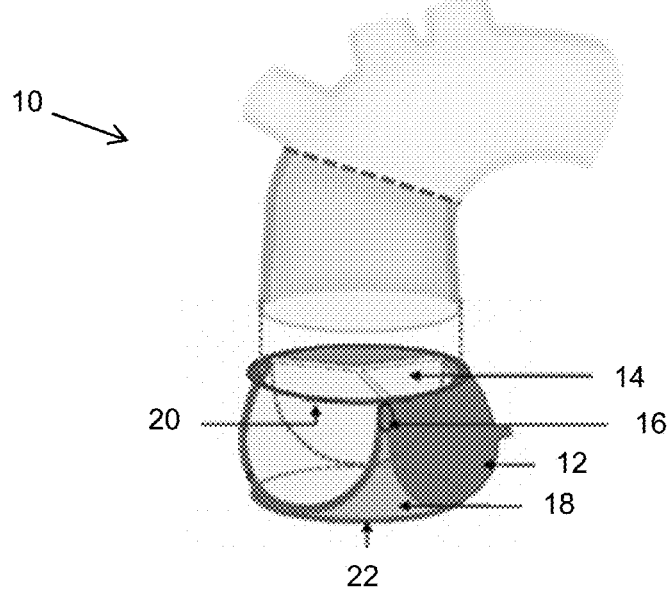
FIG. 1 is a diagram of an aortic root.

With reference to FIG. 1, an aortic root (10) comprises sinuses (12), aortic valve leaflets or cusps (14), commissures (16), interleaflet triangles (18), a sinotubular junction (20), and an annulus (ventriculo-aortic junction) (22). The cusps (14) are attached to the sinus wall along the crown-shaped annulus.

The invention provides a 3D, free-standing scaffold which is capable of both reproducing the physical properties of the natural root and attracting the appropriate type of cells. The aim is to maintain the dynamism which is believed to be essential for the function of the root, and ultimately to reproduce the native living root in vivo. The 3D scaffold consists of a hybrid of nanofibers and a support layer which can reproduce the specific physical properties of the component parts of the root.

Figure 2:
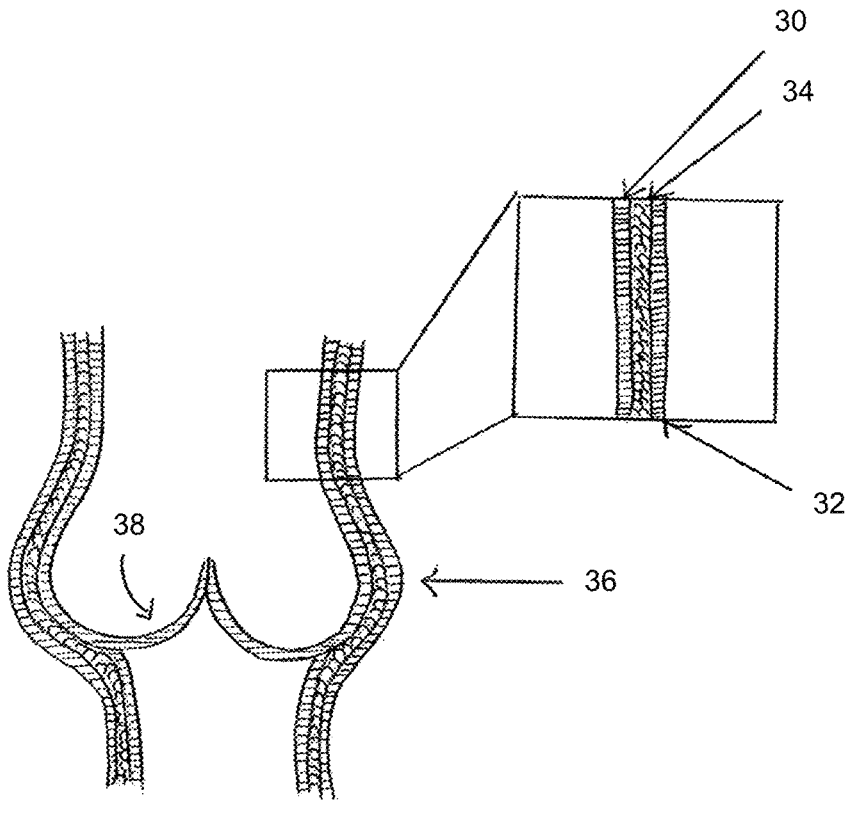
FIG. 2 is a schematic cross-sectional diagram showing the layered structure of a synthetic root in accordance with an embodiment of the invention.

FIG. 2 shows the layered structure of a synthetic root according to the invention. The synthetic root comprises inner (30) and outer (32) nanofiber layers, which may be formed from PCL by jet spraying. In these layers the fibres are circumferentially aligned. Between the nanofibers layers there is a knitted support layer (34), of varying tension. It can be seen that this multi-layered structure defines a substantially tubular shape, with a region of increased diameter (36) corresponding to the sinus regions. In the interior of the tube, leaflets (38) corresponding to cusps project inwardly into the tube. The leaflets (38) are formed from a single nanofiber layer. However, it will be appreciated that in other embodiments of the present invention the leaflets which may further comprise a support layer, such as a knitted support layer.

As will be understood by the skilled person, the curvature, shape and dimensions of the cusps and sinuses can be varied, which in turn has implications for sinus vortex development as well as helical patterns and the opening and closing of the valves. For example, the curvature of the cusps modulates the surface area of the leaflet that faces the inlet flow, which in turn enables the valve to reach its maximum opening potential. A high curvature and volume of the sinus bulges, together with a high curvature of the cusps, allows the development of a large vortex between the sinus and the leaflet, which allows the leaflet to close and coapt fully. Furthermore, optimizing the bulge shape with respect to the annulus and sino-tubular junction diameters enables healthy sinus vortex development over the cardiac cycle, particularly in late systole and early diastole to ensure healthy coronary flow supply and ensure the crucial reservoir.

FIGS. 3A and 3B are images of a knitted support layer (40) in accordance with an embodiment of the invention, while FIGS. 3C and 3D show their respective schematic diagrams. FIGS. 3A and 3C show the commissural view which shows two of the sinus bulges. FIGS. 3B and 3D show an alternative view wherein only a single bulge is visible. It can be seen from these figures that the support has an approximately tubular structure with first (42) and second (44) ends. The first end (42), shown as the upper end in the figures, is constituted by a top sewing ring, while the second end (44) is constituted by a bottom sewing ring.

Below the top sewing ring, between the ends (42, 44), three outwardly protruding portions (46) are arranged side by side, spanning the circumference of the support. Each of these portions 46 forms a bulge which corresponds in shape to the sinus of an aortic or pulmonary root. Each of the outwardly protruding portions (46) is defined by a curved lower boundary (43), which extends in the direction of the second end (44) of the support.

Beneath the outwardly protruding portions (46) which form the sinus regions, a crown-shaped region is provided, comprising three triangular portions (54) connected by a base (56) of circular cross-section. Each triangular portion (54) extends between two adjacent outwardly protruding portions (46), and corresponds to an interleaflet triangle. The bottom sewing ring (44) is located beneath the crown-shaped region.

FIGS. 4A and 4B are images of a further support layer (40) according to an embodiment of the invention. It can be seen from these figures that the knitted structure is shaped to resemble the structure of the natural root. Similarly to the support shown in FIG. 3, the support layer is substantially tubular in shape, with first (42) and second (44) ends. Between the ends a region of increased diameter is formed by three outwardly protruding portions (46), which are arranged adjacent to one another around the circumference of the tube. These protruding portions (46) correspond to the sinus regions of the root.

Each of the outwardly protruding portions (46) is partly defined by a curved edge (47) which extends in the direction of the second end (44) of the root and then curves back in the opposition direction where the edge (47) meets a junction (49), corresponding to the commissure, between adjacent protruding portions (46). Between the curved edges (47) of adjacent outwardly protruding portions (46), an approximately triangular area (54) is formed which corresponds to the interleaflet triangles. The upper boundary (50) of the outwardly protruding portions (46) corresponds to the sinotubular junction.

Between the outwardly protruding portions (46) and the first end (42), an elongate region (48) is provided with a substantially constant diameter. This region corresponds to the ascending artery.

The support layer of FIG. 4 was knitted from a PCL yarn using an industrial knitting machine, which was programmed to follow a prescribed pattern. Different tensions, knit patterns and stitches were used to confer the shape and stiffness of the different regions of the support, which include the ascending artery (48), the sinotubular junction (50), the sinus region (52), the interleaflet triangles (54), and the annulus (56). The knit pattern used is a jersey knit with tuck stitches strategically placed to follow the contours of the annulus (56). Each patterned area conveys a different region of different tension.

Example 1

A synthetic aortic root is prepared using the following method:
1) Using a dissolvable polymer such as PVA, 3D printing is used to create a mould unit A that mimics one sinus, one valve leaflet (cusp) and one third of an ascending artery, as according to a scanned image from a patient;
2) A nanofiber layer is formed on mould unit A by jet spraying a polymer solution (e.g. PCL) so as to deposit nanofibers onto the first mould unit while the first mould unit rotates at speed of 10 m/s to 50 m/s. This provides different degrees of alignment of the nanofiber, thus mimicking the anisotropic property of the valve leaflet;
3) Three individual units of nanofiber-coated mould unit A are assembled onto a 3D-printed dissolvable holder together with a single mould unit B, which mimics part of the extending artery, and a single mould unit C, which mimics the extension from the sinuses, thereby forming a complete mould having three cusps, three sinuses and the ascending artery;
4) Optionally, a nanofiber layer is formed over the complete mould by jet spraying while the assembled mould units rotate at a speed of less than 10 m/s;
5) A knitted, braided, woven or 3D-printed support layer is manufactured according to the 3D outer shape of a natural root, based on the scanned images from a patient;
6) The support layer is mounted over the nanofiber-coated mould;
7) A further nanofiber layer is formed by jet spraying to sandwich the support structure between inner and outer nanofiber layers;
8) The final construct is immersed in a solvent capable of dissolving the dissolvable polymer of the mould units, so as to remove the mould from the construct.

Example 2

A knitted support for a synthetic aortic or pulmonary root can be prepared using the following protocol:

A commercial Stoll CMS 16gg dubied, flat double bed knitting machine is used with 220 dtex PCL yarn. The pattern is designed using software M1plus. M1plus® pattern software from Stoll is the most effective solution for producing patterns for a highly-optimized knitting process. The programme suggests a knitting order for the knitting and transfer rows and these can be changed in the arrangement editor. A number of needles and rows are selected. The pattern is created in the design mode. Specific stitch types are chosen and allocated positions in selected areas.

A jersey knit pattern chosen for optimal shaping. A 1 & 1 set-up seed-tuck-gore is used for starting and ending the knit. Different tensions assigned to specific regions corresponding to the anatomical regions of the root. In an embodiment, the sewing ring has a specified tension. The sinus regions have more allocated rows and a different tension, while above the sinotubular region, the tension is again changed. Tuck stitches are inserted in specific regions. The ply is varied for certain models. A module arrangement is generated which is saved as a pattern module and sent for knitting.

The invention claimed is:
1. A synthetic root comprising a support layer having a tubular shape with first and second ends, the support layer being formed of a knitted, woven, braided or 3D-printed material, or a combination thereof, and having a region of increased diameter located between the first and second ends and a crown-shaped region located between the region of increased diameter and the second end;

at least a portion of the support layer being disposed between an inner and an outer nanofiber layer; and wherein the pattern, material, density and/or tension of the support layer in the region of increased diameter is different to that in the crown-shaped region such that the region of increased diameter and the crown-shaped region are of different stiffness;

the root further comprising one or more leaflets projecting inwardly into the tubular shape.

2. The synthetic root of claim 1, wherein the support layer is knitted.

3. The synthetic root of claim 1, wherein the support layer is formed from a yarn.

4. The synthetic root of claim 3, wherein the yarn is formed from a polymer selected from PCL, polyester, PLA, PLGA, silk (poly (dioxanone), poly (ortho esters), poly (amide esters), poly (anhydrides), polyvinyl esters, (poly (tetrafluoroethylene), poly (ethylene), poly (ethylene glycol), polypropylene oxide, or combinations thereof.

5. The-synthetic root of claim 1, wherein the region of increased diameter is formed by three outwardly protruding portions arranged around the circumference of the tube.

6. The synthetic root of claim 5, wherein the crown-shaped region comprises three triangular portions connected by a base of circular cross-section, wherein each triangular portion extends between adjacent outwardly protruding portions.

7. The synthetic root of claim 6, wherein the stiffness of the outwardly protruding portions is different to the stiffness of the crown-shaped region and/or the stiffness of other regions.

8. The synthetic root of claim 6 wherein the triangular portions comprise a hydrogel.

9. The synthetic root of claim 1, wherein the inner and/or outer nanofiber layer comprises a polymer selected from polycaprolactone (PCL), polyester, (poly(dioxanone), poly (ortho esters), esters), poly(amide poly(anhydrides), polyvinyl esters, (poly(tetrafluoroethylene), poly(ethylene), poly (ethylene glycol), polypropylene oxide, polylactic acid (PLA), poly (lactic-co-glycolic acid (PLGA), silk, or combinations thereof.

10. The synthetic root of claim 1, wherein the nanofibers of the inner and/or outer nanofiber layer are aligned.

11. The synthetic root of claim 1 wherein the inner and/or outer nanofiber layers are bound to bioactive molecules.

12. The synthetic root of claim 1, wherein the support layer has different tensions in the region of increased diameter and the crown-shaped region.

13. The synthetic root of claim 1, wherein the nanofiber layers of the leaflets have an anisotropic structure.

14. The synthetic root of claim 13, wherein the nanofiber layers of the leaflets have a different degree of alignment than nanofiber layers in other regions of the root.

15. The synthetic root of claim 1, wherein the leaflets comprise a third support layer region disposed between inner and outer nanofiber layers, and wherein the support layer of the leaflets has regions of different patterning.

\* \* \* \* \*